United States Patent [19]

Yamanis

[11] 4,365,071
[45] Dec. 21, 1982

[54] PRODUCTION OF ANHYDROUS 1,4-DIOXANE

[75] Inventor: Jean Yamanis, Lexington, Ky.

[73] Assignee: The University of Kentucky Research Foundation, Lexington, Ky.

[21] Appl. No.: 151,593

[22] Filed: May 20, 1980

[51] Int. Cl.$^3$ .............................................. C07D 319/04
[52] U.S. Cl. ..................................................... 549/377
[58] Field of Search ........................ 260/340.6; 549/377

[56] References Cited

U.S. PATENT DOCUMENTS

| | | | |
|---|---|---|---|
| 1,921,378 | 8/1933 | Webel | 260/340.6 |
| 1,939,189 | 12/1933 | Steimmig et al. | 260/340.6 |
| 2,035,386 | 3/1936 | Salzberg | 549/377 |
| 3,825,568 | 7/1974 | Schecker et al. | 549/377 |
| 3,998,848 | 12/1976 | Stapp | 549/377 |
| 4,124,541 | 11/1978 | Conrad et al. | 549/377 |
| 4,146,736 | 3/1979 | Scheffel et al. | 260/340.6 |

FOREIGN PATENT DOCUMENTS 740423  11/1955  United Kingdom ............. 260/340.6

OTHER PUBLICATIONS

Beilsteins Handbuch Organ. Chem. 19/1, p. 9, (1977).
The Canadian Journal of Chemical Engineering, vol. 57, Jun. 1979, pp. 297–304, J. Yamanis and B. D. Patton.
Chem. Abstracts 71:124349f, 76:14449j.

Primary Examiner—Ethel G. Love
Attorney, Agent, or Firm—Birch, Stewart, Kolasch & Birch

[57] ABSTRACT

This invention relates to the production of anhydrous 1,4-dioxane by the dimerization of ethylene oxide in the presence of an acidic type of cation exchanger, preferably an acidic cation exchanger resin having sulfonic acid groups associated therewith. The 1,4-dioxane is formed by contacting ethylene oxide in the liquid phase with an acidic-type cation exchanger at a first temperature and for a time sufficient to yield a reaction product of the ethylene oxide and the cation exchanger, and thereafter heating the reaction product at a second temperature higher than the first temperature and for a time period sufficient to dissociate the reaction product and thereby yield 1,4-dioxane.

13 Claims, 1 Drawing Figure

Schematic of Experimental Set-up

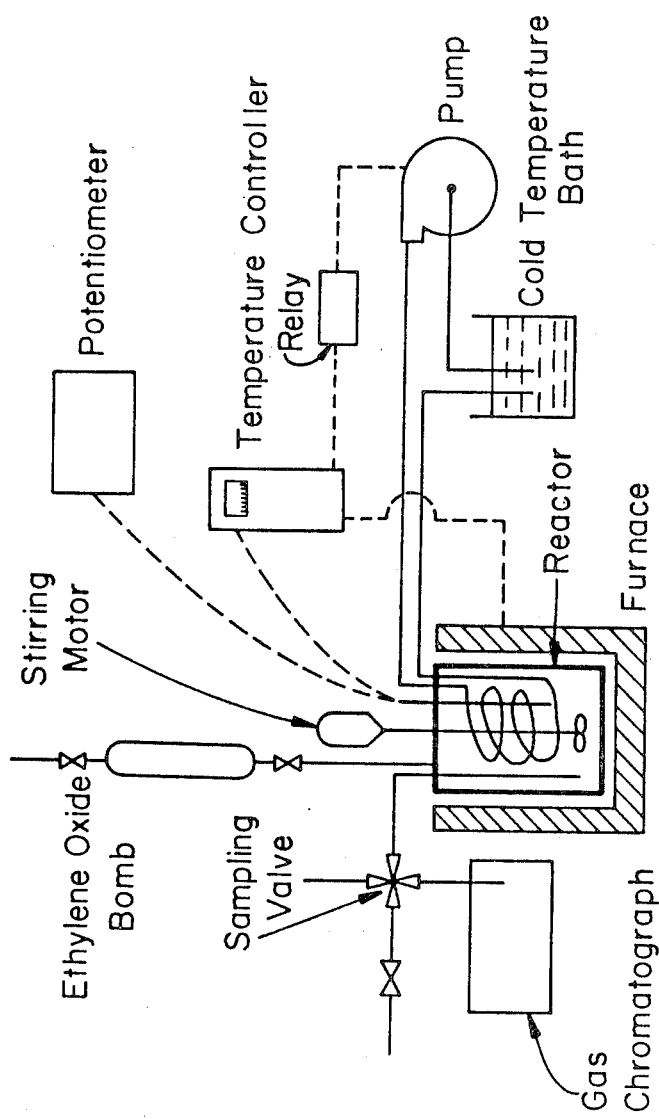
Fig. 1. Schematic of Experimental Set-up

PRODUCTION OF ANHYDROUS 1,4-DIOXANE

BACKGROUND OF THE INVENTION

This invention relates to a process for the production of anhydrous 1,4-dioxane. More particularly, the invention is concerned with a process wherein ethylene oxide is dimerized in the presence of an acidic cation exchange resin, preferably one having sulfonic acid groups associated therewith, said dimerization yielding 1,4-dioxane which is a valuable solvent.

THE PRIOR ART

Various techniques have been disclosed in the prior art for the preparation of dioxane. For example, the dimerization of an alkylene oxide to dioxane in the presence of a sulfuric acid catalyst is disclosed in U.S. Pat. No. 2,293,868 of Toussaint. U.S. Pat. No. 1,921,378 to Webel, issued on Aug. 8, 1933, discloses contacting ethylene oxide with an aluminum sulfate catalyst, resulting in the production of dioxane.

More recent disclosures include U.S. Pat. No. 3,825,568 to Schecker et al, issued on July 23, 1974, which teaches the dimerization of ethylene oxide to dioxane in the presence of various Lewis acid catalysts, e.g., $ZnCl_2$, $SnCl_4$, $SiF_4$, and $BF_3$. Canadian Patent No. 540,278 to Astle et al, issued on Apr. 30, 1957, shows the preparation of dioxane by contacting various polyethylene glycols with various acidic type cation exchangers, e.g., sulfonated polystyrene type resins, sulfonated phenol-formaldehyde type resins, etc. British Patent No. 785,229 to Petrochemicals, Ltd., published Oct. 23, 1957, teaches the dimerization of ethylene oxide to dioxane in the presence of a metal alkyl catalyst, e.g., aluminum triethyl.

A process is also known for preparing dioxane by contacting diethylene glycol with sulfo-acid cationites, i.e., cation exchanger resins containing sulfonic acid groups.

However, all of these techniques suffer from one or more disadvantages which has prevented an effective commercialization of this process to date.

The dimerization of ethylene oxide for the production of 1,4-dioxane is a known reaction, and, as noted above, various proposals have been advanced in the prior art in an attempt to bring this reaction within the field of practical utility by executing it in the presence of catalysts. Several catalysts for this purpose are of an acidic nature, particularly sulfuric acid and salts thereof such as aluminum sulfate, and also various Lewis acids such as $ZnCl_2$, $SnCl_4$, etc.

While the processes which depend upon the employment of acidic catalysts have the advantage of permitting the use of simple apparatus, they are still quite undesirable from the commercial standpoint. Under the reaction conditions employed in the prior art, the acidic reaction mixtures have a strongly corrosive action on the reaction equipment, making necessary the use of costly non-corrosive apparatus or requiring periodic replacement of the initially less costly apparatus. Many processes of this kind make use of sulfuric acid as the catalyst and involve elimination of the acid, after the dimerizing reaction is terminated, e.g., by precipitating it from the reaction mixture in the form of its barium or calcium salts. Such separation is, however, always incomplete, and substantial amounts of non-precipitatable salts of organic sulfuric acid compounds remain in the reaction mixture which are only separated during distillation and cause contamination of the desired product. Besides the inconveniences mentioned, executing the reactions in the presence of acid catalysts results in material losses and contaminated products due to the occurrence of side reactions. Thus, for example, when sulfuric acid is employed as the catalyst, there is always produced, due to side reactions, a greater or lesser amount of tars which are only difficultly separably from the reaction mixture.

SUMMARY OF THE INVENTION

Therefore, the primary object of the present invention is to provide a practical and economical process which is adapted to the technical scale production of 1,4-dioxane by dimerizing ethylene oxide in the presence of an acidic cation exchange resin. Another objective of the invention is to provide an efficient process for producing anhydrous 1,4-dioxane.

The process of the present invention makes it possible to eliminate the drawbacks and inconveniences of the known processes for effecting the dimerization of ethylene oxide to produce 1,4-dioxane. This process is based on the use of an acidic cation exchange resin which accelerates the rate of reaction to at least as great an extent as any of the catalysts previously employed. Therefore, although the cation exchange resins are not catalysts in accordance with the precise meaning of the term as such, these materials are referred to as "catalysts" herein for the sake of convenience. The catalysts employed in this invention are readily available and can be easily and completely removed after completion of the dimerization reaction without any destruction of the reaction product. As a result, the process of the invention provides excellent yields of the desired reaction product, with the reaction proceeding smoothly and rapidly at considerably lower temperatures and under lower pressures than are necessary when operating in the presence of the known acidic catalysts. Although the catalysts employed in the invention can be discarded after the dimerization is completed, they can also be easily regenerated by a simple procedure as described below.

DESCRIPTION OF THE DRAWING

Other objects and advantages of the present invention will become apparent from a study of the following description and the accompanying drawing in which the FIGURE is a schematic representation of the experimental set-up used in the invention.

DETAILED DESCRIPTION OF THE INVENTION

These objectives are accomplished by the process of the present invention which comprises dimerizing ethylene oxide in the presence of an acidic cation exchange resin, preferably one having sulfonic acid groups associated therewith. The reaction mechanism involved in conducting this process is believed to be as follows:

STAGE I

In this stage, a reaction is carried out between the ethylene oxide and the cation exchange resin containing sulfonic acid groups to form an ester:

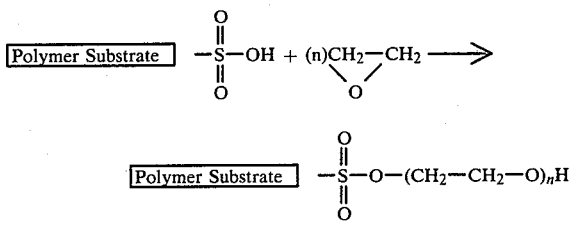

wherein n ≧ 1. (The average value of n is about 2.4)

It is apparent that, in this stage, the ethylene oxide reacts with the sulfonic acid groups of the resin to form ester species on the resin which involve chains of several ethylene oxide units.

STAGE II

In this stage, the ester is thermally dissociated with the following reactions at a temperature in excess of that at which said ester was initially formed.

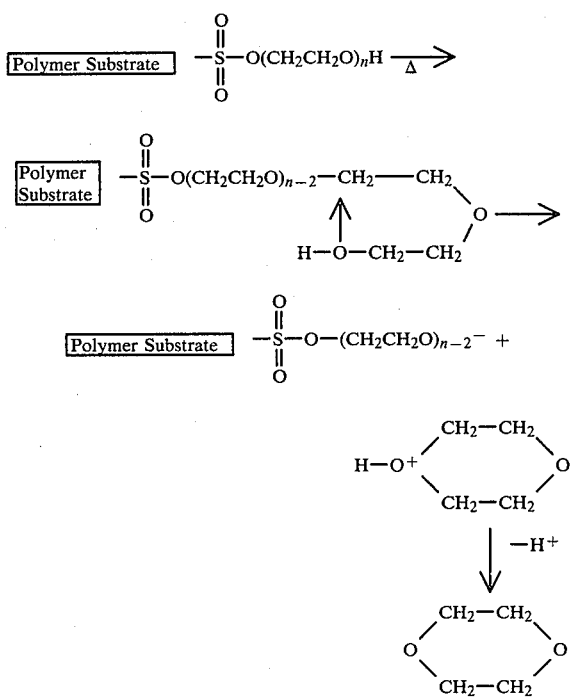

In this second stage, the dioxane formation is effected by the back-biting of the chain to product oxonium species which liberate 1,4-dioxane and an $H^+$. Other reactions are possible during this stage of the process.

THE CATALYST EMPLOYED

It has been found that the dimerization of the ethylene oxide to form 1,4-dioxane proceeds at a practical, rapid rate with resultant high yields of the desired product if it is conducted in the liquid phase in the presence of an acidic cation exchange resin, preferably one having sulfonic acid groups associated therewith. Suitable acidic cation exchange resins for use according to the process of this invention are, for example, the sulfonated coal-type resins such as "Zeo-Karb" made by the Permutit Co., the sulfonated phenol-formaldehyde resins such as "Amberlite IR-120", and the sulfonated styrene-divinyl benzene type resins such as "Amberlyst 15" manufactured by the Rohm and Haas Co., the sulfonated phenolic type resins such as "Duolite" made by the Chemical Process Co., and the sulfonated polystyrene-type resins such as "Dowex 50" made by the Dow Chemical Co. In addition to resins having a sulfonic polar group, resins such as those having carboxylic, phenolic, or phosphoric polar groups are also suitable. As an example of this type of resin there may be mentioned the acidic cation exchanger having carboxylic acid groups, i.e., —COOH, associated therewith. A discussion as to the preparation of this type of acidic cation exchanger is to be found in U.S. Pat. No. 2,597,437 to Bodamer, issued on May 20, 1952. Other patents directed to this type of acidic cation exchanger are U.S. Pat. Nos. 2,340,110 and 2,340,111.

Resins, and especially those with medium porosity or macroreticular structure, having sulfonic acid groups are preferred for the dimerization of ethylene oxide in accordance with the invention. Resins having phosphonic or phosphinic acid groups essentially behave like the sulfonic acid resins because bonding in sulfur and phosphorous compounds is very similar and, for this reason, sulfonic and phosphonic acid groups are known to behave in a similar manner in many organic reactions. For example, the acid anions of these groups are suitable leaving groups in the hydrolysis of esters of the form $RSO_2OCH_3$ and $RPO(OH)OCH_3$. Cation exchange resins with carboxylic acid groups also react with ethylene oxide to yield polymeric esters.

The following table contains a listing of exermplary ion exchange resins which may be employed in the present invention.

Table of the Most Common Commercial Ion Exchangers*
Cation Exchangers

| Matrix | Ionic group | Trade name | Manufacturer | Capacity meq/g dry resin | Capacity meq/ml resin bed | Moisture content, % wt | Maximum temperature, °C | pH range | Physical form | Remarks |
|---|---|---|---|---|---|---|---|---|---|---|
| Polystyrene resins | $-SO_3^-$ | Amberlite IR-120 | Rohm & Haas Co.[+] | 4.3-5 | 1.9 | 44-48 | 120 | 0-14 | Spherical beads | Standard resin, ca. 8% DVB |
| | | Amberlite IR-122 | Rohm & Haas Co.[+] | 4.3-5 | 2.1 | 40-44 | 120 | 0-14 | Spherical beads | ca. 10% DVB, higher resistance to oxidizing agents |
| | | Amberlite IR-124 | Rohm & Haas Co.[+] | 4.3-5 | 2.1 | 37-41 | 120 | 0-14 | Spherical beads | ca. 12% DVB, higher resistance to oxidizing agents |
| | | Amberlite 200 | Rohm & Haas Co.[+] | 4.3 | 1.75 | 47-52 | 120 | 0-14 | Spherical beads | Higher mech. and chem. stability, lower capacity |
| | | Amberlite XE-100 | Rohm & Haas Co.[+] | 4.5 | 1.2 | 58-65 | 120 | 0-14 | Spherical beads | ca. 4% DVB |
| | | Amberlyst 15 | Rohm & Haas Co.[+] | 4.9 | 1.2 | 60-66 | 120 | 0-14 | Spherical beads | "Macroreticular" resin |
| | | Dowex 50 | Dow Chemical Co.[++] | 4.9-5.2 | Depends on crosslinking | | 150 | 0-14 | Spherical beads | Available with different degrees of crosslinking (Dowex 50-X2 has 2% DVB, etc.); Dowex 50W is improved resin replacing older Dowex 50 |
| | | Dowex 50W | Dow Chemical Co.[++] | 4.9-5.2 | | | 150 | 0-14 | Spherical beads | |
| | | Duolite C-20 | Chemical Process Co. | 5.1 | 2.2 | 45-51 | 150 | 0-14 | Spherical beads | Standard resin, ca. 8% DVB; other degrees of crosslinking on request |
| | | Duolite C-25 | Chemical Process Co. | 5.1 | 1.7 | 55-62 | 120 | 0-14 | Spherical beads | Porous resin |
| | | Duolite C-27 | Chemical Process Co. | 5.0 | 2.1 | 45-50 | 150 | 0-14 | Spherical beads | Resin of lighter color |
| | | Imac C-12 | "Activit," Holland | 4.5 | 2 | | 120 | 0-14 | Spherical beads | Standard resin, ca. 8% DVB |
| | | Imac C-19 | "Activit," Holland | 4.5 | 1.4 | | 120 | 0-14 | Spherical beads | Porous resin |
| | | Ionac C-240 | (Permutit Q, marketed by Ionac Co.) | | | | | | | |
| | | Lewatit S-100 | Farbenfabriken Bayer, Germany (West) | 4.75 | 2.5 | 40-45 | 110 | 0-12 | Spherical beads | Standard resin, ca. 8% DVB |
| | | Lewatit S-115 | Farbenfabriken Bayer, Germany (West) | 4.6 | 2.4 | 40-45 | 110 | 0-12 | Spherical beads | Higher resistance to oxidizing agents |
| | | Nalcite HCR | (Dowex 50-X8, marketed by Nalco Chemical Co.) | | | | | | | |
| | | Nalcite HGR | (Dowex 50-X10, marketed by Nalco Chemical Co.) | | | | | | | |
| | | Nalcite HDR | (Dowex 50-X12, marketed by Nalco Chemical Co.) | | | | | | | |
| | | Permutit Q | Permutit Co., U.S.A. | 4.8 | 2.0 | 45-50 | 120 | 0-14 | Spherical beads | Standard resin; other degrees on crosslinking available |
| | | Permutit RS | Permutit A. G., Berlin, Germany (West) | 5.5 | | | 150 | | Spherical beads | |
| | | Resex P | Jos. Crosfield, England | | | | | | Spherical beads | |
| | | Wofatit KPS | VEB Farbenfabrik Wolfen, Germany (East) | 4.5 | | | 115 | | Spherical beads | Standard resin with 10% DVB; resins with 2, 4, 6, and 16% DVB also available |

-continued
Table of the Most Common Commercial Ion Exchangers*
Cation Exchangers

| Matrix | Ionic group | Trade name | Manufacturer | Capacity meq/g dry resin | Capacity meq/ml resin bed | Moisture content, % wt | Maximum temperature, °C | pH range | Physical form | Remarks |
|---|---|---|---|---|---|---|---|---|---|---|
| | | Zeo-Karb 225 | Permutit Co. Ltd., England** | 4.8 | 2.1 | 45–50 | 120 | | Spherical beads | Standard resin with 8% DVB; resins with 1, 2, 4.5, 12, and 20% DVB also available |
| | $-PO_3^{2-}$ | Bio-Rex 63 Duolite ES-61 | (Duolite C-63, analytical grade, marketed by Bio-Rad Laboratories) Chemical Process Co. | | | | | 4–14 | Spherical beads | Experimental resin |
| | | Duolite C63 | Chemical Process Co. | 6.6 | 3.1–3.3 | | | 4–14 | Spherical beads | Experimental resin, ca. 6% DVB, more porous than ES-61 |
| | | Nalcite X-219 | Nalco Chemical Co. | | | | | 4–14 | Spherical beads | Experimental resin |
| | $-HPO_2^-$ | Bio-Rex 62 Duolite ES-60 | (Duolite C-62, analytical grade, marketed by Bio-Rad Laboratories) Chemical Process Co. | | | | | 4–14 | Spherical beads | Experimental resin |
| | | Duolite C-62 | Chemical Process Co. | 6.0 | 2.6 | | | 4–14 | Spherical beads | Experimental resin, more porous than ES-60 |
| | $-N(CH_2COOH)_2$ | Chelex 100 Dowex A-1 | (Dowex A-1, analytical grade, marketed by Bio-Rad Laboratories) Dow Chemical Co. | 1–1.2 | 0.33 | 71–76 | | 4–14 | Spherical beads | Chelating resin |
| Vinyl addition polymers | $-OSO_3^-$ | CFB-P | Chem. Fabrik Budenheim, Germany (West) | | | | 100 | | Spherical beads | |
| | $-COOH$ | Amberlite IRC-50 | Rohm & Haas Co. + | 9.5 | 3.5 | 43–53 | 120 | 5–14 | Spherical beads | |
| | | Amberlite XE-89 | Rohm & Haas Co. + | 7.9 | 4.2 | 52–60 | 120 | 5–14 | Spherical beads | |
| | | Bio-Rex 70 Duolite CS-101 | (Duolite CS-101, analyt. grade, marketed by Bio-Rad Laboratories) Chemical Process Co. | 10 | 3.5 | | 100 | 6–14 | Spherical beads | Special resin for pharmaceutical applications |
| | | Ionac C-270 Permutit C | (Permutit H-70, marketed by Ionac Co.) Permutit A. G., Berlin, Germany (West) | 10 | 4 | | 100 | 6–14 | Spherical beads | |
| | | Permutit H-70 | Permutit Co., New York | 7.9 | 3.6 | | 95 | 6–14 | Spherical beads | |
| | | Wofatit CP | VEB Farbenfabrik Wolfen, Germany (East) | 10 | | | 30 | | Spherical beads | |
| | | Zeo-Karb 226 | Permutit Co. Ltd., England** | 10 | 3.5 | 45–50 | 100 | | Spherical beads | Available with 2.5 and 4.5% crosslinking |
| Phenolic resins | $-SO_3^-$ | Bio-Rex 40 Duolite C-3 | (Duolite C-3, analytical grade, marketed by Bio-Rad Laboratories) Chemical Process Co. | 2.9 | 1.2 | | 60 | 0–9 | Granules | |
| | | Duolite C-10 | Chemical Process Co. | 2.9 | 0.6 | | 40 | 0–9 | Granules | Resins with $-CH_2SO_3^-$ groups; C-10 more porous than C-3 |
| | | Lewatit KSN | Farbenfabriken Bayer, Germany (West) | 4.0 | 1.6 | | 30 | 0–8 | Granules | |
| | | Wofatit F | VEB Farbenfabrik Wolfen, Germany (East) | 2.9 | | | 50 | | Granules | |
| | | Wofatit P | | 1.9 | | | 35 | | Granules | |

-continued
Table of the Most Common Commercial Ion Exchangers*
Cation Exchangers

| Matrix | Ionic group | Trade name | Manufacturer | Capacity meq/g dry resin | Capacity meq/ml resin bed | Moisture content, % wt | Maximum temperature, °C | pH range | Physical form | Remarks |
|---|---|---|---|---|---|---|---|---|---|---|
| | | Zeo-Karb 215 | Permutit Co. Ltd., England** | 2.6 | 0.9 | | 40 | | Granules | —SO$_3^-$ groups |
| | —PO$_3^{2-}$ | Duolite ES-65 | Chemical Process Co. | 3.3 | 1.4 | | | | Granules | Experimental resin |
| | —COOH | Duolite CS-100 | Chemical Process Co. | 1.9 | 0.8 | | | | Granules | |
| | | Ionac C-265 | (Permutit H, marketed by Ionac Co.) | | | | | | | |
| | | Lewatit CNO | Farbenfabriken Bayer, Germany (West) | 4.0 | 2.5 | 30-35 | 40 | 0-8 | Granules | |

*Properties given are manufacturers' data and are not strictly comparable since testing procedures differ.
†Amberlite resins (A.R. and C.P. grades) are also marketed by Mallinckrodt.
†† Dowex resins (analytical grade) are also marketed by Bio-Rad Laboratories.
**Zeo-Karb and De-Acidite resins are also marketed under the name Zerolit (with otherwise same designation) by United Water Softeners, London.

A high catalytic activity of the acidic cation exchange resins makes it attractive to employ them in the process of the invention since only small amounts are required in order to obtain a substantial yield of the 1,4-dioxane in a relatively short period of time. The actual amount of catalyst needed in the process, however, is dependent upon a number of factors, including the particular apparatus in which the reaction is carried out, and the operating conditions employed. Satisfactory results may be obtained by utilizing about 0.08 to 4.7 grams of catalyst per gram of ethylene oxide reactant.

In the case of one of the preferred resins, such as Amberlyst 15(H+), a suitable amount to be employed is about 0.2 grams of resin per gram of ethylene oxide. Of course, a greater amount of catalyst may be employed, if desired. A smaller amount may also be suitable.

With respect to the amount of acidic cationic resin to be employed, it is to be noted that a rough approximation thereof is also possible, by stoichiometric calculation, if the exchange capacity of the resin is known, i.e., the number of mmol of the acid group per gram of dry resin.

The catalyst present in the final reaction mixture can be preliminarily separated, for example, by filtration, and recovery of the 1,4-dioxane from the liquid phase can then be effected. Alternatively, the recovery of the 1,4-dioxane from the final reaction mixture can be effected while the catalyst is still present therein. This recovery of the reaction product may be effected in any suitable manner. In most cases, it is conveniently done by distillation, preferably under subatmospheric pressure. The catalyst, however recovered, can if desired be regenerated simply by boiling in a sodium hydroxide solution, followed by treatment to convert it from the sodium form to the acid form.

OPERATING PARAMETERS

It has now been found that the production of anhydrous 1,4-dioxane by dimerization of ethylene oxide in the presence of an acidic cation exchange resin, preferably one having sulfonic acid groups associated therewith, can be carried out advantageously and with high yields (approximately 95%) by mixing the catalyst with ethylene oxide in the liquid phase and keeping the resultant mixture at a temperature in the range of about $-20°$ C. to 90° C., preferably about 25° C., for a time period of about 5 to 200 minutes. Thereafter, the reaction mixture is heated to a temperature in the range of about 80° C. to 140° C., preferably about 90° C. to 120° C., keeping the reaction mixture in the liquid phase. The reaction mixture is then kept at this temperature for a period of about 60 to 300 minutes in order to effect the formation of 1,4-dioxane in high yield.

When the process is carried out as described above only one by-product is formed and this in very minor amounts. This contrasts sharply with the large amounts of by-products of a tarry nature which are formed when the dimerization is carried out in the presence of a sulfuric acid catalyst.

In accordance with this invention, the ethylene oxide is used in the liquid phase, i.e., in the form of pure ethylene oxide or dissolved in a solvent which is inert under the reaction conditions utilized.

Suitable solvents are those which are liquid under the reaction conditions, which do not react either with ethylene oxide or with the catalyst and which do not form with the 1,4-dioxane an azeotrope which interferes with the subsequent processing operations. Examples of such solvents are organic solvents such as isopropyl ether, benzene, cyclohexane, pentane, chlorobenzene, and ethylene chloride. The 1,4-dioxane itself may be used as the solvent in both stages of reaction with the advantage of greatly simplifying the separation steps.

The reaction is generally carried out at atmospheric pressure. However, pressures of up to 30 atmospheres may also be used.

The reaction may be carried out batchwise or continuously. All reactors which ensure adequate residence times, thorough mixing and adequate control of reaction temperature may be employed. For example, in batchwise operation, stirred vessels or shaker autoclaves may be used having an external or internal reaction temperature control means.

The reaction mixture is advantageously worked up in the usual manner. Separation of the solid spent catalyst from the reaction mixture can be effected by filtration, etc. Thereafter, the components of the liquid part of the reaction mixture can be separated, for example, by fractional distillation, etc.

The process of the invention gives anhydrous 1,4-dioxane in a simple way and in very good product yields. The process may be carried out on an industrial scale without great expenditure.

1,4-Dioxane is an excellent solvent for many organic compounds and is distinguished by the fact that it is miscible in all proportions with water and the usual organic solvents.

EXAMPLES OF THE INVENTION

The following examples are given merely as illustrative of the present invention and are not to be considered as limiting.

EXAMPLES 1, 2 and 3

The dimerization of ethylene oxide in the presence of a cation exchange resin was carried out in a one liter stainless steel reactor. This reactor was equipped with a liquid sampling tube which extended to within 1.5 cm. from the bottom of the reactor. A stainless steel sintered filter was attached to the end of the sampling line to prevent resin from leaving the reactor during sampling. An explosion-proof electric motor stirred the system at a rate of 435 r.p.m. The temperature of the reaction system was controlled to within $\pm 1.0°$ C. by a PID temperature controller. The system was equipped with a shielded copper Constantan thermocouple which allowed the temperature to be monitored using a potentiometer.

In a typical run a weighed quantity of vacuum-oven dried resin was loaded and sealed in the reactor. The reactor was flushed with gaseous nitrogen and evacuated several times to remove any air present. After the final evacuation, the inert solvent, i.e., chlorobenzene (99% pure, Aldrich Chemical Co., Inc.), in an amount sufficient to bring the total reaction mixture to 800 ml at room temperature, was sucked into the reactor, and the reactor was heated to reaction temperature under stirring. Ethylene oxide for the dimerization was transferred from a commercial cylinder to a stainless steel bomb in the required amount. The ethylene oxide bomb was connected to the reactor and pressurized with nitrogen which discharged the oxide into the reactor. As the ethylene oxide was charged, the system pressure was raised to the desired level using nitrogen gas. The reaction was run for a specified length of time and immediately after the reacted resin was separated from the reaction fluid. The reacted resin was then washed with acetone in a separatory funnel, dried using a stream of nitrogen gas, and weighed. The difference between the masses of reacted and dried resin was the amount of ethylene oxide reacted on the resin.

The reacted resin was subsequently suspended in a solvent, e.g., chlorobenzene, and brought to reaction temperature for the production of dioxane. The data for some runs are shown in Table 1. A schematic of the experimental apparatus used for making these reaction runs is shown in FIG. 1.

During the second stage reaction, the reaction fluid was sampled using a 4-port sampling valve and analyzed using a gas chromatograph. 1,4-Dioxane was quantitatively determined using a 20 ft. by ⅛ in. O.D. column packed with 10% FFAP on Chromosorb WAW (supplied by Johns-Manville). Nitrogen carrier gas was employed at the rate of 30 ml/min, measured at the column exit and room temperature. The injection port and detector temperatures were set at 240° C., while the oven temperature program was 2 minutes at 80° C., and then the temperature was raised to 165° C. at 20°/min and maintained at 165° C. for 10 minutes. Peak areas were determined using a digital integrator, and quantitative results were obtained using response factors.

TABLE 1

| | Dimerization of Ethylene Oxide to 1,4-Dioxane | | | | | | | |
|---|---|---|---|---|---|---|---|---|
| Example No. | Ethylene Oxide Used[1] (g) | Ethylene Oxide Reacted (g) | Resin (g) | Initial Reaction Temperature | Initial Reaction Time (min) | Final Reaction Temperature (°C.) | Final Reaction Time (min.) | 1,4-Dioxane (g) |
| 1 | 163.3 | 11.7 | Amberlyst 15 (H+) 39.1 g[2] | Room Temp. | 15 | 110 | 390 | 11.04 |
| 2 | 151.2 | 9.40 | Amberlyst 15 (H+) 20.6 g | Room Temp. | 15 | 120 | 226 | 8.62 |
| 3 | 151.8 | 5.96[4] | Amberlite IR-120 (H+) 31.1 g[3] | Room Temp. | 180 | | | |

[1] 99.9+ percent pure- Procured from Air Products and Chemicals, Inc.
[2] Amberlyst 15 (H+) procured from Rohm and Haas. Macroreticular resin with average pore diameter of about 180 Angstrom units, average surface area of 47 m²/g. dry resin and total exchange capacity of 4.8 mmols of —SO₃H groups per g. dry resin.
[3] Amberlite IR-120 (H+) procured from Rohm and Haas. Total exchange capacity is 5.36 mmols of —SO₃H groups per g. dry resin.
[4] Less than half of —SO₃H groups were esterified. Reaction for the experimental conditions reported was incomplete.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A process for the preparation of 1,4-dioxane which comprises contacting ethylene oxide in the liquid phase with an effective amount of an acidic cation exchange resin at a first temperature and for a time sufficient to yield an ester intermediate reaction product of said ethylene oxide and said cation exchange resin, and thereafter heating said ester intermediate reaction product at a second temperature higher than said first temperature and for a time period sufficient to dissociate said reaction product and thereby yield 1,4-dioxane.

2. A process for the preparation of 1,4-dioxane which comprises contacting ethylene oxide in the liquid phase with an effective amount of an acidic cation exchange resin at a temperature in the range of about −20° C. to 90° C. and for a time period of about 5 minutes to 200 minutes to yield an ester intermediate reaction product of said ethylene oxide and said cation exchange resin, thereafter heating said ester intermediate reaction product at a higher temperature of about 80° C. to 140° C. and for a time period of about 60 minutes to 300 minutes, and then recovering the 1,4-dioxane formed as a result of said heating.

3. A process as recited in claims 1 or 2 in which the acidic cation exchange resin is a cation exchange resin having a porous or macroreticular structure and having acid groups associated therewith.

4. A process as recited in claim 3 wherein the acid groups are selected from the group consisting of sulfonic, phosphonic, phosphinic, carboxylic and mixtures thereof.

5. A process as recited in claim 4 in which the cation exchange resin has sulfonic acid groups associated therewith.

6. A process as recited in claim 4 wherein the cation exchange resin is a sulfonated polystyrene resin.

7. A process as recited in claim 6 in which the cation exchanger is a sulfonated styrene-divinyl benzene resin.

8. A process as recited in claims 1 or 2 in which the reaction is carried out at pressures from atmospheric up to about 30 atmospheres.

9. A process as recited in claims 1 or 2 in which the reaction is carried out in a solvent which is inert under the reaction conditions employed.

10. A process as recited in claim 9, wherein said solvent is selected from the group consisting of isopropyl ether, benzene, cyclohexane, pentane, chlorobenzene, ethylene chloride, 1,4-dioxane and mixtures thereof.

11. A process as recited in claim 5 wherein the cation exchange resin is regenerated by boiling in a sodium hydroxide solution.

12. A process according to claim 9, wherein the solvent is an organic solvent.

13. A process according to claim 10, wherein the solvent is 1,4-dioxane.

* * * * *